US010034943B2

(12) United States Patent
Herslöf et al.

(10) Patent No.: US 10,034,943 B2
(45) Date of Patent: Jul. 31, 2018

(54) SPRAYABLE TOPICAL CARRIER AND COMPOSITION COMPRISING PHOSPHATIDYLCHOLINE

(71) Applicant: LIPIDOR AB, Stockholm (SE)

(72) Inventors: Bengt Herslöf, Stockholm (SE); Jan Holmbäck, Vaxholm (SE)

(73) Assignee: LIPIDOR AB, Stockholm (SE)

(*) Notice: Subject to any disclaimer, the term of this patent is extended or adjusted under 35 U.S.C. 154(b) by 0 days.

(21) Appl. No.: 15/036,183

(22) PCT Filed: Nov. 6, 2014

(86) PCT No.: PCT/SE2014/051313
§ 371 (c)(1),
(2) Date: May 12, 2016

(87) PCT Pub. No.: WO2015/072909
PCT Pub. Date: May 21, 2015

(65) Prior Publication Data

US 2016/0303239 A1    Oct. 20, 2016
US 2017/0360937 A9    Dec. 21, 2017

Related U.S. Application Data

(63) Continuation-in-part of application No. 14/114,778, filed as application No. PCT/SE2012/000061 on Apr. 30, 2012, now abandoned.

(30) Foreign Application Priority Data

May 2, 2011   (SE) ..................................... 1100340
Nov. 14, 2013 (SE) ..................................... 1300710

(51) Int. Cl.

| A61K 8/58 | (2006.01) |
| A61K 47/14 | (2017.01) |
| A61K 8/34 | (2006.01) |
| A61K 47/24 | (2006.01) |
| A61K 8/37 | (2006.01) |
| A61K 47/10 | (2017.01) |
| A61K 9/08 | (2006.01) |
| A61K 8/55 | (2006.01) |
| A61Q 19/00 | (2006.01) |
| A61K 9/12 | (2006.01) |
| A61K 8/365 | (2006.01) |
| A61K 8/42 | (2006.01) |
| A61K 8/49 | (2006.01) |
| A61K 9/00 | (2006.01) |
| A61K 31/137 | (2006.01) |
| A61K 31/165 | (2006.01) |
| A61K 31/192 | (2006.01) |
| A61K 31/196 | (2006.01) |
| A61K 31/245 | (2006.01) |
| A61K 31/351 | (2006.01) |
| A61K 31/4174 | (2006.01) |
| A61K 31/506 | (2006.01) |
| A61K 31/573 | (2006.01) |
| A61K 31/59 | (2006.01) |
| A61K 31/593 | (2006.01) |
| A61K 31/60 | (2006.01) |
| A61K 38/08 | (2006.01) |
| A61K 38/10 | (2006.01) |
| A61K 38/17 | (2006.01) |
| A61Q 7/00 | (2006.01) |

(52) U.S. Cl.
CPC ............... *A61K 47/24* (2013.01); *A61K 8/34* (2013.01); *A61K 8/365* (2013.01); *A61K 8/37* (2013.01); *A61K 8/375* (2013.01); *A61K 8/42* (2013.01); *A61K 8/4953* (2013.01); *A61K 8/553* (2013.01); *A61K 8/585* (2013.01); *A61K 9/0014* (2013.01); *A61K 9/08* (2013.01); *A61K 9/12* (2013.01); *A61K 31/137* (2013.01); *A61K 31/165* (2013.01); *A61K 31/192* (2013.01); *A61K 31/196* (2013.01); *A61K 31/245* (2013.01); *A61K 31/351* (2013.01); *A61K 31/4174* (2013.01); *A61K 31/506* (2013.01); *A61K 31/573* (2013.01); *A61K 31/59* (2013.01); *A61K 31/593* (2013.01); *A61K 31/60* (2013.01); *A61K 38/08* (2013.01); *A61K 38/10* (2013.01); *A61K 38/1729* (2013.01); *A61K 47/10* (2013.01); *A61K 47/14* (2013.01); *A61Q 7/00* (2013.01); *A61Q 19/00* (2013.01); *A61K 2800/592* (2013.01)

(58) Field of Classification Search
None
See application file for complete search history.

(56) References Cited

U.S. PATENT DOCUMENTS

| 6,267,985 B1 * | 7/2001 | Chen ..................... A61K 9/0095 424/43 |
| 2003/0170194 A1 * | 9/2003 | Piotrowiak ............ A61K 8/046 424/70.12 |
| 2007/0041910 A1 * | 2/2007 | Pitre ..................... A61K 9/0014 424/45 |

FOREIGN PATENT DOCUMENTS

| CN | 101146509 A | 3/2008 |
| WO | WO2011/056115 A1 | 5/2011 |

(Continued)

OTHER PUBLICATIONS

International Preliminary Report on Patentability for PCT Patent App. No. PCT/SE2014/051314 (dated May 17, 2016).

(Continued)

*Primary Examiner* — Ernst V Arnold
*Assistant Examiner* — Kyung S Chang
(74) *Attorney, Agent, or Firm* — Cermak Nakajima & McGowan LLP; Malcolm K. McGowan

(57) ABSTRACT

A pharmaceutical or cosmetic carrier for topical administration substantially consists of phosphatidylcholine, monoglyceride, fatty acid ester of $C_1$-$C_3$ alcohol; volatile solvent selected from ethanol and its combinations with $C_3$-$C_4$ alcohol and/or volatile silicone oil. Also disclosed are pharmaceutical and cosmetic compositions comprising the carrier and pharmaceutically or cosmetically active agent(s).

27 Claims, No Drawings

(56) References Cited

FOREIGN PATENT DOCUMENTS

| WO | WO2011/056116 A1 | 5/2011 |
| WO | WO2012/150892 A1 | 11/2012 |
| WO | WO2014/178789 A1 | 11/2014 |

OTHER PUBLICATIONS

International Search Report for PCT Patent App. No. PCT/SE2014/051313 (dated Feb. 24, 2015).

Written Opinion for PCT Patent App. No. PCT/SE2014/051313 (dated Feb. 24, 2015).

Bonina, F. P., et al., "In vitro and in vivo evaluation of polyoxyethylene esters as dermal prodrugs of ketoprofen, naprozen and diclofenac," Eur. J. Pharm. Sci. 2001;14:123-134.

Duval, C., et al., "Differences among moisturizers in affecting skin susceptibility to hexyl nicotinate, measured as time to increase skin blood flow," Skin Res. Tech. 2003;9:59-63.

Niren, K., et al., "Enhancement of bioavailability by lowering of fat content in topical formulations," Br. J. Dermatol. 2009;160:552-556.

\* cited by examiner

SPRAYABLE TOPICAL CARRIER AND COMPOSITION COMPRISING PHOSPHATIDYLCHOLINE

CROSS-REFERENCE TO RELATED APPLICATIONS

This application is a national stage entry under 35 USC 371 of international application PCT/SE2014/051313, filed 6 Nov. 2014, which claims priority from Swedish patent application 1300710-9, filed 14 Nov. 2013. This application also claims priority to U.S. patent application Ser. No. 14/114,778, filed 30 Oct. 2013, now abandoned, which was a national stage entry under 35 USC 371 of PCT/SE2012/000061, filed 30 Apr. 2012, which claims priority from Swedish patent application 1100340-7, filed 5 Feb. 2011. The contents of these applications are incorporated herein in their entirety.

FIELD OF THE INVENTION

The present invention relates to a carrier for pharmaceutically and/or cosmetically active agents and to pharmaceutical and cosmetic compositions for topical administration comprising the carrier and pharmaceutically or cosmetically active agents.

BACKGROUND OF THE INVENTION

Pharmaceutical compositions for topical administration are of two kinds: one kind aiming at administering a pharmaceutically active agent onto healthy or diseased skin to produce its effect on the skin and/or in one or more layers of the skin, the other kind aiming at the delivery of a pharmaceutically active agent through the skin. Cosmetic compositions are designed for topical administration onto healthy skin and for producing their effect on the skin.

WO 2011/056115 discloses a lipid carrier composition, comprising or substantially consisting of polar lipid, volatile silicone oil, and a lower alcohol.

OBJECTS OF THE INVENTION

It is an object of the invention to provide a liquid pharmaceutical or cosmetic composition for topical administration of a pharmaceutically or cosmetically active agent, respectively, to the skin of a person or an animal, which is easily administrable and capable of forming a coherent lipid layer on the skin. It is desirable that the aforementioned composition exhibits one or more of the following features upon application to the skin:

re-establishment of the protective barrier of the skin if applied to skin if said barrier has been compromised; and/or lack of skin irritation.

Other objects of the invention include providing a carrier for a pharmaceutically or cosmetically active agent intended for administration to the skin of a person or an animal and a method for incorporating the active agent into the carrier so as to form a topical pharmaceutical or cosmetic composition. Further objects of the invention will be evident from the following summary of the invention, preferred embodiments thereof described in form of examples, and from the appended claims.

SUMMARY OF THE INVENTION

According to the present invention is disclosed a pharmaceutical or cosmetic carrier for topical administration substantially consisting of phosphatidylcholine, monoglyceride, fatty acid ester of $C_1$-$C_3$ alcohol and volatile solvent comprising ethanol. The carrier may optionally comprise one or more members of the group consisting of antioxidant, colorant, odorant, preservative, and denaturant.

More particularly, the pharmaceutical or cosmetic carrier of the invention for topical administration consists substantially of: phosphatidylcholine; monoglyceride; fatty acid ester of $C_1$-$C_3$ alcohol; volatile solvent selected from the group consisting of: ethanol; ethanol and $C_3$-$C_4$ alcohol; ethanol and volatile silicone oil; ethanol, $C_3$-$C_4$ alcohol and volatile silicone oil; wherein the carrier optionally comprises one or more members of the group consisting of antioxidant, colorant, odorant, preservative, and denaturant.

Phosphatidylcholine of the invention can be natural or synthetic. Natural phosphatidylcholine includes enriched phospholipid from soybeans (soy lecithin, soy-PC, for example Lipoid S 100 and Lipoid S 75), sunflower or rapeseed, containing at least 50% by weight of phosphatidylcholine, the remainder consisting mainly of other polar lipids (such as phosphatidylethanolamine, phosphatidylglycerol, phosphatidylinositol and galactolipids) and acylglycerols (monoacylglycerols, diacylglycerols and triacylglycerols). Examples of synthetic phosphatidylcholine comprise dioleoyl phosphatidylcholine and dimyristoyl phosphatidylcholine.

In this application "on the skin" includes the outermost layer of the skin, the stratum corneum. A pharmaceutical or cosmetic composition of the invention is designed for topical administration to the skin including to interstices in the stratum corneum.

According to the present disclosure, "vehicle" is synonymous with "carrier".

Commercially available monoglycerides suitable for use in the invention comprises mixtures of monoacylglycerol with diglycerides (diacylglycerol) and/or triglycerides (triacylglycerol). Examples of monoglycerides include, but are not limited to, medium chain monoglycerides containing 40% by weight or more of $C_8$-$C_{10}$ monoacylglycerol and monoolein containing 50% by weight or more of monooleoylglycerol. Preferred fatty acid esters of the invention are isopropyl myristate, isopropyl palmitate, ethyl oleate and methyl laurate.

In addition to ethanol, the volatile solvent of the invention may comprise one or more of $C_3$-$C_4$ alcohol, such as isopropanol and n-butanol, and volatile silicone oil, such as cyclomethicone 5-NF (decamethylcyclopentasiloxane) and/or, less preferred dodecamethylcyclohexasiloxane and/or decamethyltetrasiloxane. All components of the volatile solvent have a boiling point of 200° C. or less at ambient pressure (1 atm), except for volatile silicone oil, which may have a boiling point at 1 atm of up to 250° C. Preferred silicone oils have boiling points in the range of 180-250° C. at 1 atm.

Into the pharmaceutical carrier of the invention may be incorporated one or more pharmaceutically active agents, whereby a pharmaceutical composition for topical administration is formed. The composition of the invention is intended to efficiently deliver the active agent into the skin and is neither intended nor useful for transdermal delivery of a pharmaceutically active agent. The one or more pharmaceutically active agent of the invention is selected from the group consisting of: antimicrobial agent, antibiotic; antimycotic agent; antibacterial agent; antifungal agent; antiviral agent; antiseptic; anti-phlogistic; anti-pruritic agent; anti-psoriatic agent; antitussive agent; anti-alopecia agent; anti-acne agent; anti-inflammatory agent; analgesic; antiulcer agent; local anaesthetic; and immune response modifying agent.

More particularly, the pharmaceutically active agent of the invention is selected from: antibacterial agents, such as oxytetracycline, fusidic acid, gentamycine, mupirocin, retapamulin (and pharmaceutically acceptable salts and derivatives thereof); antimycotic agents, such as nystatin, clotrimazole, miconazole, econazole, ketoconazole, bifonazole, and combinations of imidazole and triazole derivatives, ciclopirox, terbinafine, fluconazole, and amorolfine (and pharmaceutically acceptable salts and derivatives thereof); antiviral agents, such as aciclovir, valaciclovir, penciclovir, famciclovir, foscarnet (trisodium phosphonoformate hexahydrate) and docosanol (and pharmaceutically acceptable salts and derivatives thereof); antiseptics, such as chlorhexidine, benzalkonium chloride and hydrogen peroxide; anti-inflammatory agents (glucocorticoids), such as hydrocortisone, clobetasone, triamcinolone, betamethasone, mometasone, and clobetasol (and pharmaceutically acceptable salts and derivatives thereof); antiphlogistics/analgesics, such as acetylsalicylic acid, salicylic acid, diclofenac, ketoprofen, ibuprofen, naproxen, capsaicin, nicotinate (and pharmaceutically acceptable salts and derivatives thereof); antipruritic agents, such as glucocorticoids, for example, hydrocortisone, clobetasone, clobetasol, desonide, mometasone and betamethasone, and local anaesthetics, for example, lidocaine and prilocaine (and pharmaceutically acceptable salts and derivatives thereof); antipsoriatic agents, such as calcipotriol, calcitriol, 7-dehydrocholesterol, cholecalciferol, maxacalcitol, doxercalciferol, paricalcitol, inecalcitol, eldecalcitol, betamethasone and cyclosporine A (and pharmaceutically acceptable salts and derivatives thereof); agents for treatment of eczema and atopic dermatitis: tacrolimus and pimecrolimus (and pharmaceutically acceptable salts and derivatives thereof); antiglaucomateous agents, such as timolol, betaxolol, latanoprost, bimatoprost, and travoprost (and pharmaceutically acceptable salts and derivatives thereof); local anaesthetics, such as lidocaine, prilocaine, ropivacaine, mepivacaine, bupivacaine, levobupivacaine, benzocaine, and tetracaine (and pharmaceutically acceptable salts and derivatives thereof); agents for erectile dysfunction, such as alprostadil (prostaglandin E1) (and pharmaceutically acceptable salts and derivatives thereof); anti-dandruff agents, such as selenium sulphides, piroctone oleamine and ketoconazole; anti-alopecia agents, such as minoxidil (and pharmaceutically acceptable salts and derivatives thereof); anti-acne agents, such as tretinoin (retinoic acid), isotretinoin, adapalene, benzoyl peroxide, clindamycin, azelaic acid, niacinamide (and pharmaceutically acceptable salts and derivatives thereof); wound healing agents, such as pantothenic acid, dexpanthenol and fusidic acid (and pharmaceutically acceptable salts and derivatives thereof); steroid hormones, such as prednisone, dexamethasone, triamcinolone, fludrocortisone, testosterone, estradiol, distilbestrol; and peptide hormones, such as oxytocin, LL-37, DPK-060 and PXL-01 (and pharmaceutically acceptable salts and derivatives thereof).

According to an embodiment, the at least one pharmaceutically active agent is calcipotriol, betamethasone (or esters thereof), hydrocortisone (or esters thereof), mometasone furoate and/or diclofenac (or salts thereof).

An antioxidant of the invention is any additional component that inhibits other components from degrading due to oxidation. Antioxidants are exemplified by, but not limited to, reducing agents such as thiols, ascorbic acid, or polyphenols, free radical scavengers such as tocopherols (Vitamin E) and tocotrienols, sequestering agents such as EDTA and phosphonates, or organic acids such as acetic acid, glycolic acid or lactic acid. A person skilled in the art understands which colorants, odorants and preservatives are suitable for a carrier according to the present invention.

A denaturant as defined in this disclosure is an agent or mixture of agents making the composition of the invention unattractive for human consumption. Examples of denaturants are esters of phthalic acid, 2-isopropyl-5-methyl-phenol, denatonium benzoate, 3-methyl-cyclopentadecanone, ethyl acetate and their combinations. $C_3$-$C_4$ alcohols may be a part of the denaturant system but in the context of the invention they are comprised by the volatile solvent described herein. At room temperature (20° C.), a convenient temperature for administration, the carrier and the composition of the invention are single-phase homogeneous liquids. They are preferably administered to the skin by spraying. For administration any spraying pump suitable for topical administration of liquid compositions can be used. Evaporation of the volatile solvent from the skin leaves a coherent layer thereon. The layer so formed lacks a greasy feeling, reduces water loss through the skin, and re-establishes the protective skin barrier if compromised.

The carrier and the compositions of the invention are well tolerated by healthy and irritated human skin.

After evaporation of the solvent the non-volatile components of the carrier and the compositions of the invention form a continuous, single phase layer on the skin that reduces water loss through the skin.

A pharmaceutically active agent comprised by the composition of the invention may be any agent suitable for treating a skin condition amenable to topical treatment.

The composition of the invention is particularly useful for treating inflammatory conditions, such as atopic dermatitis. Hydrocortisone is a preferred pharmaceutically active agent for treating erythema that can be incorporated into the carrier of the invention and can be comprised by the composition of the invention. Diclofenac is another preferred pharmaceutically active agent for treating inflammation of the skin that can be incorporated into the carrier of the invention and can be comprised by the composition of the invention.

The pharmaceutical composition of the invention is also particularly useful for treating psoriasis. Calcipotriol is a preferred pharmaceutically active agent for treating psoriasis that can be incorporated into the carrier of the invention and can be comprised by the composition of the invention.

According to a first aspect of the invention, there is provided a pharmaceutical or cosmetic carrier for topical administration substantially consisting of:
phosphatidylcholine;
monoglyceride;
fatty acid ester of $C_1$-$C_3$ alcohol;
volatile solvent selected from the group consisting of:
ethanol; ethanol and $C_3$-$C_4$ alcohol; ethanol and volatile silicone oil; ethanol, $C_3$-$C_4$ alcohol and volatile silicone oil;
wherein the carrier optionally comprises one or more members of the group consisting of antioxidant, colorant, odorant, preservative and denaturant.

According to an embodiment of the invention, the carrier comprises:
from 2% or 5% to 15% or 20% or 25% or 30% or 40% by weight of phosphatidylcholine;
from 2% or 5% to 15% or 20% or 25% by weight of monoglyceride;
from 2% or 5% to 15% or 20% or 25% or 30% by weight of fatty acid ester of $C_1$-$C_3$ alcohol;

the remainder being ethanol at a concentration of at least 25%, the ethanol optionally comprising one or several of:

i) up to 20% or 30% or 40% or even up to 50% by weight of $C_3$-$C_4$ alcohol;

ii) up to 50% or 60% or even 75% by weight of volatile silicone oil;

iii) up to 1% by weight of antioxidant, colorant, odorant, preservative, and denaturant.

According to an embodiment, the amount of ethanol in a carrier of the invention is in the range of 20% to 90% by weight.

According to an embodiment, the amount of $C_3$-$C_4$ alcohol in a carrier of the invention is in the range of 1% to 20% by weight.

According to another embodiment, the ethanol of the carrier comprises up to 50% of isopropanol.

According to yet another embodiment, the amount of volatile silicone oil in a carrier of the invention is in the range of 10% to 55% by weight.

According to one embodiment, the carrier comprises up to 2% of denaturant.

Decamethylcyclopentasiloxane is a preferred volatile silicone oil of the carrier of the invention.

The pharmaceutical composition of the invention consists substantially of:

a) from 90% or 95% or 98% and up to 99.999% by weight of the pharmaceutical carrier of the invention;

b) from 0.001% or 0.1% to 2% or 5% or exceptionally up to 10% by weight of at least one pharmaceutically active agent.

According to a preferred embodiment, the pharmaceutical composition of the invention consists of a carrier (a):

a) from 90% or 95% or 98% and up to 99.999% by weight of carrier consisting of:

from 2% or 5% to 15% or 20% or 25% or 30% or 40% by weight of phosphatidylcholine;

from 2% or 5% to 15% or 20% or 25% by weight of monoglyceride;

from 2% or 5% to 15% or 20% or 25% or 30% by weight of fatty acid ester of $C_1$-$C_3$ alcohol;

the remainder being ethanol of a concentration of at least 25%, the ethanol optionally comprising one or several of:

i) up to 20% or 30% or 40% or even up to 50% by weight of $C_3$-$C_4$ alcohol;

ii) up to 50% or 60% or even 75% by weight of volatile silicone oil, iii) up to 1% by weight of antioxidant, colorant, odorant, preservative and denaturant;

and b) from 0.001% or 0.1% to 2% or 5% or exceptionally up to 10% by weight of at least one pharmaceutically active agent; wherein the weight portions of carrier and at least one pharmaceutically active agent in the composition are adding up to 100%.

According to one embodiment, the pharmaceutical composition comprises up to 2% denaturant.

Decamethylcyclopentasiloxane is a preferred volatile silicone oil of the pharmaceutical composition of the invention.

The cosmetic composition of the invention substantially consists of:

a) from 90% or 95% or 98% and up to 99.999% by weight of the cosmetic carrier of the invention, and b) from 0.001% or 0.1% to 2% or 5% or exceptionally up to 10% by weight of one or more cosmetically active agents.

The weight portions of carrier and one or more cosmetically active agent in the composition are adding up to 100%.

According to a preferred embodiment, the cosmetic composition of the invention substantially consists of a carrier (a):

a) from 90% or 95% or 98% and up to 99.999% by weight of carrier consisting of:

from 2% or 5% to 15% or 20% or 25% or 30% or 40% by weight of phosphatidylcholine;

from 2% or 5% to 15% or 20% or 25% by weight of monoglyceride;

from 2% or 5% to 15% or 20% or 25% or 30% by weight of fatty acid ester of $C_1$-$C_3$ alcohol;

the remainder being ethanol of a concentration of at least 25%, the ethanol optionally comprising one or several of:

i) up to 20% or 30% or 40% or even up to 50% by weight of $C_3$-$C_4$ alcohol;

ii) up to 50% or 60% or even 75% by weight of volatile silicone oil;

iii) up to 1% by weight of antioxidant, colorant, odorant, preservative, and denaturant;

and b) from 0.001% or 0.1% to 2% or 5% or exceptionally up to 10% by weight of one or more cosmetically active agent; wherein the weight portions of carrier and at least one cosmetically active agent in the composition are adding up to 100%.

According to an embodiment, the cosmetic composition comprises up to 2% of denaturant.

According to an embodiment, the ethanol of the pharmaceutical composition comprises up to 50% of isopropanol Decamethylcyclopentasiloxane and decamethyltetrasiloxane are preferred volatile silicone oils of the cosmetic composition of the invention.

The cosmetically active agent of the invention may be any agent suitable for cosmetic use capable of being incorporated into the cosmetic carrier of the invention. Preferred cosmetically active agents of the invention comprise: antiperspirants, such as aluminium chlorohydrate; sun screens, such as avobenzone, bemotrizinol, diethylamino hydroxybenzoyl hexyl benzoate, octisalate, octocrylene, oxybenzone; tanning agents, such as dihydroxyacetone; insects repellants, such as Deet; keratolytics, such as glycolic acid, lactic acid, malic acid, salicylic acid, allantoin, urea and sulphur; antidandruff agents; glidants; moisturizing agents, such as glycerol, sorbitol, dexpanthenol, propylene glycol, butandiols, pentanediols, hexanediols, urea and lactic acid.

According to one embodiment, the one or more cosmetically active agents is selected from urea, glycolic acid, lactic acid, glycerol, propylene glycol and dexpanthenol.

The pharmacological and cosmetic compositions of the invention can be prepared by dissolving pharmaceutically active agent or cosmetic agent, respectively, in the carrier or in one or more components of the carrier followed by preparing the carrier by mixing its components.

According to an embodiment, a spraying device comprises a composition of the present invention and optionally a driving gas.

DESCRIPTION OF PREFERRED EMBODIMENTS

Material and Methods
Lipids Used in the Examples:

| Short name | Supplier, trade name | Chemical name | CAS No. |
|---|---|---|---|
| S-75 | Lipoid S 75 | Soybean phospholipid | 8030-76-0 |
| S-100 | Lipoid S 100 | Soybean phospholipid | 97281-47-5 |
| DMPC | Lipoid DMPC | Dimyristoyl phosphatidylcholine | 13699-48-4 |
| DOPC | Lipoid DOPC | Dioleoyl phosphatidylcholine | 10015-85-7 |
| H-100 | Lipoid H 100 | Sunflower phosphatidylcholine | 97281-47-5 |
| H-50 | Lipoid H 50 | Sunflower lecithin | 8002-43-5 |
| Monoolein | Fluka (Sigma-Aldrich), Monoolein | Monooleoylglycerol | 25496-72-4 |
| MCM | Abitec Corporation, Capmul MCM C8 EP | Medium chain monoglycerides, Glycerol monocaprylate | 26402-26-6 |
| IPM | Aldrich, Isopropyl myristate | Isopropyl myristate | 110-27-0 |
| IPP | Aldrich, Isopropyl palmitate | Isopropyl palmitate | 142-91-6 |
| Methyl laurate | Aldrich, Methyl laurate | Methyl laurate | 111-82-0 |
| Ethyl oleate | Aldrich, Ethyl oleate | Ethyl oleate | 111-62-6 |

Alcohols used in the examples were ethanol 99.9% ("EtOH", VWR), 2-propanol (isopropanol, HPLC grade, Rathburn), and 2-butanol (ReagentPlus®, Sigma-Aldrich). The silicone oils used in the examples were Cyclomethicone 5-NF ("5-NF", Dow Corning, decamethylcyclopentasiloxane) and decamethyltetrasiloxane ("DMTS", Dow Corning).

Pharmacologically and cosmetically active agents and excipients used in the formulation experiments (with CAS Nos) were adapalene (106685-40-9), ascorbic acid (50-81-7), benzocaine (94-36-0), betamethasone dipropionate (5593-20-4), benzyl nicotinate (94-44-0), betamethasone valerate (2152-44-5), butylhydroxytoluene (128-37-0), calcipotriol (112965-21-6), capsaicin (404-86-4), citric acid (77-92-9), clindamycin hydrochloride (21462-39-5), curcumin (458-37-7), dexpanthenol (81-13-0), diclofenac sodium (15307-79-6), econazole nitrate (24169-02-6), glycolic acid (79-14-1), hydrocortisone (50-23-7), hydrocortisone acetate (50-03-3), ibuprofen (15687-27-1), ketoprofen (22071-15-4), lactic acid (50-21-5), methyl nicotinate (93-60-7), minoxidil (38304-91-5), mometasone furoate (83919-23-7), mupirocin (12650-69-0), naproxen (22204-53-1), oxytocin acetate (50-56-6), peptide LL-37 (human cathelicidin), propylene glycol (57-55-6), salicylic acid (69-72-7), sodium fusidate (751-94-0), tacrolimus (104987-11-3), terbinafine hydrochloride (78628-80-5), urea (57-13-6) and vitamin $D_3$ (cholecalciferol, 67-97-0). Peptide LL-37 was from Lipopeptide AB (Solna, Sweden) and all other substances from Sigma-Aldrich.

The formulation experiments were performed according to the following general procedure. The lipids were weighed and dissolved in ethanol or a mixture of ethanol and other alcohols of the invention. In some experiments complete dissolution of the lipids was promoted by short ultrasonication in a bath-type sonicator at about 30-40° C. Pre-weighed amounts of active agent(s) and additive(s) were added to the vehicle. According to the present invention, the term "vehicle" is synonymous with "carrier". In some experiments the mixture was gently heated and sonicated until a clear solution was formed. The alcoholic solution of lipids was optionally diluted with volatile silicone oil. The thus obtained yellow to brownish solutions were stored in airtight glass vials at room temperature.

The effect of prior art pharmaceutical compositions and of carriers and compositions of the invention on human skin was observed by visual inspection or by determining erythema index by using DermaLab Combo and DSM II Colormeter (Cortex Technology, Denmark).

Measurements of methyl nicotinate induced erythema were used to study the skin barrier function and the impact on vehicle on the delivery of active ingredients according to methods known in the art (Bonina F P et al., *In vitro and in vivo evaluation of polyoxyethylene esters as dermal prodrugs of ketoprofen, naproxen and diclofenac*. Europ J Pharm Sci 14 (2001) 123-134; Duval C et al., *Difference among moisturizers in affecting skin susceptibility to hexyl nicotinate, measured as time to increase skin blood flow*. Skin Res Techn 9 (2003) 59-63; Wiren K et al., *Enhancement of bioavailability by lowering of fat content in topical formulations*. Br J Dermat 160 (2009) 552-556). An alcoholic or glycerol/water solution of methyl nicotinate (in some cases benzyl nicotinate) was applied to areas on the skin either after pretreatment with test formulation or followed by application of the test formulation. Skin color was measured based on an active color detecting chip where illumination is provided by white LEDs and the measured parameter (erythema index, E.I.) corresponds to the redness of the skin (Bonina F P et al., supra). Area under the curve (AUC) was calculated as the area between the measured E.I and the baseline.

The invention is described by the following non-limiting examples.

Example 1. Occurrence of Erythema Upon Treating Skin with Carrier of the Invention Under Occlusion for 12 Days Erythema occurrence was assessed in two human studies. In the first study the skin irritation potential of different lipid carriers was evaluated. Thirty-three healthy volunteers received the test formulations and a positive and negative control under occlusive conditions. The test articles were applied 5 days per week and the irritation grade was scored after 12 days according to a four-level assessment index (0=No reaction; 1=Slight diffuse, partial erythema; 2=Clear, sharply demarcated erythema; 3=Severe erythema with induration; 4=Severe erythema with induration and/or epidermal defect). Mean assessment indices for the different treatments are presented in Table 1.

For the negative control petrolatum and the two phosphatidylcholine containing vehicles (C and D) almost no occurrence of erythema was observed, whereas for the IPM (A) and MCM (B) containing vehicles a slightly higher mean assessment index was found. For the positive control, sodium dodecylsulfate 0.25%, a mean assessment index of 3.0 was obtained.

In a second study with the primary objective to evaluate the effect of calcipotriol compositions on plaque psoriasis, the adverse reaction of lipid carriers was also monitored. The test procedure and treatment schedule was identical to the first study, and the number of patients was twentyfour. After 12 days treatment erythema was not observed in any of the patients which had received the vehicle of the invention E, whereas, in the first study, slight erythema had been observed in some of the patients treated with petrolatum and other carriers (A through D) not comprised by the invention.

TABLE 1

Erythema caused by different carriers after occlusive treatment for 12 days

| Components | Pos. control | Petrolatum | A | B | C | D | E* |
|---|---|---|---|---|---|---|---|
| Isopropyl myristate | | | 20 | — | — | — | 5 |
| Medium chain monoglycerides | | | — | 20 | — | — | 5 |
| Dimyristoyl phosphatidylcholine | | | — | — | 20 | — | — |
| Soybean lecithin, containing 50% or more of phosphatidylcholine | | | — | — | — | 20 | 10 |
| Ethanol | | | 20 | 20 | 20 | 20 | 20 |
| Cyclomethicone 5-NF | | | 60 | 60 | 60 | 60 | 60 |
| Sodium dodecylsulfate | 0.25 | | | | | | |
| Mean erythema assessment index | 3.0 | 0.03 | 0.31 | 0.13 | 0.06 | 0.06 | 0 |

*Carrier of the invention.

Example 2. Nicotinate Induced Erythema Development Upon Application of Various Lipid Vehicles Circular areas (3.5 cm$^2$) were marked on the volar parts of both forearms of healthy male persons. Baseline measurements of skin color (erythema index, E.I.) were made on the test areas. 5 µl of a 0.2% methyl nicotinate ethanolic solution and thereafter 5 µl of the vehicles were evenly distributed on the test areas by the use of a micropipette. E.I. was measured for about two hours. Carrier 8 of the invention decreased erythema index in respect of the carriers 7 and 9. These data indicate that the combination of isopropyl myristate, monoglyceride and phosphatidylcholine (carrier G) is dampening erythema formation.

TABLE 2

Effect of carriers nos. F, G and H on nicotinate-induced erythema

| Components | F | G* | H |
|---|---|---|---|
| Isopropyl myristate | | 5.3 | 9.9 |
| Medium chain monoglycerides | | 5.2 | 9.8 |
| Phosphatidylcholine | 20.3 | 9.5 | |
| Ethanol | 29.8 | 29.8 | 29.5 |
| Cyclomethicone 5-NF | 50.0 | 50.5 | 51.0 |

TABLE 2-continued

Effect of carriers nos. F, G and H on nicotinate-induced erythema

| Components | F | G* | H |
|---|---|---|---|
| AUC of ΔE.I. (erythema 0-2 hours) | 5.2 | 4.6 | 5.1 |

*Carrier of the invention

Example 3. Erythema Development after Skin Pre-Treatment with Hydrocortisone Compositions The effect of skin pre-treatment with hydrocortisone compositions on subsequent nicotinate induced erythema was studied. Circular areas (3.5 cm$^2$) were marked on the volar parts of both forearms of healthy male persons. 5 µl of a prior art hydrocortisone composition (ointment) and a composition according to the invention were evenly distributed on the test areas by the use of a micropipette. After pre-treatment with the compositions for 2 h, baseline measurements of skin color (erythema index, E.I.) were made on the test areas. Erythema was induced by applying 5 µl of a 0.4% methyl nicotinate ethanolic solution on the test areas followed by E.I. measurements over two hours. The composition of the invention dampened erythema development in comparison with the commercial ointment.

TABLE 3

Effect of pretreatment with hydrocortisone compositions on erythema development

| Compositions. Components in % by weight | AUC of ΔE.I. (erythema 0-2 hours) |
|---|---|
| Hydrocortisone 1% ointment (CCS, Sweden)** | 5.4 |
| Hydrocortisone 1% in: IPM 12.4%, MCM 13.4%, Lipoid S 100 24.4%, EtOH 49.0%* | 3.4 |

*Composition of the invention.
**Prior art

Example 4. Erythema Treatment by Diclofenac Formulations Compared to the Vehicles The effect of treatment with diclofenac compositions on areas with methyl nicotinate induced erythema was compared to the effect of the corresponding carriers, using a procedure similar to the one described in Example 2. All compositions reduced erythema more than their vehicles (Table 5). Composition 2 of the invention comprising a phosphatidylcholine, isopropyl myristate, and medium chain monoglyceride showed the highest erythema reducing effect. The corresponding carrier of the invention (Carrier 2) reduced erythema more than Carriers 1 and 3.

TABLE 4

Treatment of nicotinate induced erythema by diclofenac compositions and corresponding carriers

| Components | Carrier #1** | Comp. #1** | Carrier #2* | Comp. #2* | Carrier #3** | Comp. #3** |
|---|---|---|---|---|---|---|
| Diclofenac sodium | — | 1.3 | — | 1.3 | — | 1.3 |
| Isopropyl myristate | — | — | 5.3 | 4.9 | 9.9 | 10.0 |

TABLE 4-continued

Treatment of nicotinate induced erythema by diclofenac
compositions and corresponding carriers Composition or carrier. Components in % by weight

| Components | Carrier # 1 | Comp. # 1 | Carrier # 2* | Comp. # 2* | Carrier # 3 | Comp. # 3 |
|---|---|---|---|---|---|---|
| Medium chain monoglyceride | — | — | 5.2 | 4.9 | 9.8 | 10.0 |
| Lipoid S 100 | 20.3 | 20.2 | 9.5 | 10.2 | — | — |
| Ethanol | 29.8 | 28.7 | 29.8 | 28.6 | 29.5 | 28.8 |
| Cyclomethicone 5-NF | 50.0 | 49.8 | 50.5 | 50.1 | 51.0 | 50.0 |
| AUC of ΔE.I. (erythema 0-2 h) | 5.2 | 3.8 | 4.6 | 3.5 | 5.1 | 4.2 |

*Carrier or composition of the invention;
**Carrier or composition not comprised by the invention

Example 5. Erythema Treatment by Diclofenac Compositions Compared to a Known Commercial Composition Areas with benzyl nicotinate induced erythema were treated with diclofenac compositions and compared to Voltaren® Gel (11.6 mg/ml), using a procedure similar to the one described in Example 2. Compositions C2 and C4 of the invention reduced erythema more than Voltaren® Gel (Table 5).

TABLE 5

Erythema treatment by administration of diclofenac
compositions of the invention and of a state-of-
the-art commercial diclofenac composition

| Components, in % by weight | Compositions | | |
|---|---|---|---|
| | Voltaren ® Gel ** | C2 * | C4 * |
| Diclofenac | 1.2 | 1.3 | 1.3 |
| Isopropyl myristate | — | 4.9 | 4.9 |
| Medium chain monoglyceride | — | 4.9 | 4.9 |
| Lipoid S 100 | — | 10.2 | 9.9 |
| Ethanol | — | 28.6 | 78.9 |
| Cyclomethicone 5-NF | — | 50.1 | — |
| AUC of ΔE.I. (erythema 0-2 hours) | 4.6 | 3.2 | 3.8 |

* Compositions of the invention.
** Prior art composition

Example 6. Erythema Treatment with Hydrocortisone and Ketoprofen Compositions Areas with methyl nicotinate induced erythema were treated with a hydrocortisone composition of the invention and a commercial ointment, using a procedure similar to the one described in Example 2. The composition of the invention provided a better effect than the commercial product (Table 6). Similarly, a ketoprofen composition of the invention was compared with a commercial hydrophilic gel product. The formulation of the invention provided a slightly better effect than the known product (Table 6).

TABLE 6

Treatment of nicotinate induced erythema with
hydrocortisone and ketoprofen compositions

| Compositions. Components in % by weight | AUC of ΔE.I. (erythema 0-2 h) |
|---|---|
| Hydrocortisone 1% ointment (CCS, Sweden)** | 4.4 |
| Hydrocortisone 1% in: IPM 12.4%, MCM 13.4%, Lipoid S 100 24.4%, EtOH 49.0%* | 2.3 |
| Orudis gel (Ketoprofen 2.5%)** | 3.0 |
| Ketoprofen 1.9% in: IPM 12.1%, MCM 13.9%, Lipoid S 100 24.5%, EtOH 47.5%* | 2.7 |

*Composition of the invention.
**Prior art composition.

Example 7. Psoriasis Plaque Test after Treatment with Calcipotriol Formulations In a clinical study a calcipotriol composition of the invention (C6) was compared to a commercial calcipotriol solution (Daivonex®) and to a corresponding composition lacking phosphatidylcholine. The composition of the invention C6 resulted in the highest plaque reduction (Table 7).

TABLE 7

Change in mean plaque thickness after 12 days treatment
with a commercial calcipotriol composition (Daivonex ® solution)
and calcipotriol formulations C5 and C6

| Component | Daivonex ® solution** | C5** | C6 * |
|---|---|---|---|
| | Component % by weight | | |
| Calcipotriol | 0.005 | 0.005 | 0.005 |
| Isopropyl myristate | — | 10.0 | 5.0 |
| Medium chain monoglycerides | — | 10.0 | 5.0 |
| Lipoid S 75 | — | — | 10.0 |
| Ethanol | — | 20.0 | 20.0 |
| Cyclomethicone 5-NF | — | 60.0 | 60.0 |
| Mean change in plaque thickness after 12 days treatment (μm) | −161 | −179 | −185 |

* Composition of the invention.
**Prior art composition or composition not comprised by the invention Example 8. Examples of Carriers and Compositions of the Invention Examples of carriers of the invention are shown in Table 8.

TABLE 8

Carriers of the invention based on Lipoid S 100

| Carrier | IPM | MCM | Lipoid S 100 | Ethanol | Cyclomethicone 5-NF |
|---|---|---|---|---|---|
| | | | Components % by weight | | |
| a | 5 | 10 | 15 | 70 | |
| b | 10 | 5 | 15 | 70 | |
| c | 5 | 5 | 10 | 80 | |
| d | 12.5 | 12.5 | 25 | 50 | |
| e | 10 | 10 | 20 | 30 | 30 |
| f | 5 | 5 | 10 | 30 | 50 |
| g | 5 | 5 | 10 | 20 | 60 |

Examples of pharmaceutical compositions of the invention are shown in Tables 9-17 and examples of carriers in Table 18.

TABLE 9

Pharmaceutical compositions of the invention based on Lipoid S 75

| Active agent | Agent | Lipoid S 75 | IPM | MCM | Ethanol | Cyclomethicone 5-NF | Water |
|---|---|---|---|---|---|---|---|
| | | | Components, % by weight | | | | |
| Benzocaine | 5.10 | 9.9 | 5.2 | 5.1 | 19.9 | 54.8 | |
| Minoxidil | 0.45 | 10.2 | 5.1 | 5.2 | 19.9 | 59.3 | |
| Hydrocortisone acetate | 0.13 | 10.7 | 5.3 | 5.8 | 19.6 | 58.5 | |
| Capsaicin | 1.01 | 9.9 | 4.9 | 4.8 | 20.1 | 59.2 | |
| Mupirocin | 0.22 | 10.3 | 5.1 | 5.2 | 19.6 | 59.5 | |
| Betamethasone valerate | 0.09 | 10.7 | 4.8 | 5.1 | 20.1 | 59.3 | |
| Betamethasone dipropionate | 0.10 | 8.1 | 3.0 | 5.2 | 83.6 | | |
| Terbinafine HCl | 0.98 | 10.4 | 4.5 | 5.3 | 20.0 | 58.9 | |
| Econazole nitrate | 0.98 | 9.8 | 4.8 | 7.0 | 19.7 | 57.7 | |
| Vitamin $D_3$ | 0.012 | 10.3 | 5.5 | 5.3 | 19.9 | 59.0 | |
| Salicylic acid | 1.04 | 10.8 | 5.0 | 4.9 | 19.8 | 58.5 | |
| Peptide LL-37 | 0.22 | 10.1 | 5.0 | 5.2 | 19.9 | 58.8 | 0.8 |
| Oxytocin acetate | 0.019 | 9.9 | 4.9 | 7.2 | 19.0 | 57.8 | 1.2 |

TABLE 10

Pharmaceutical compositions of the invention based on Lipoid S 100

| Active agent | Agent (% w/w) | Lipoid S 100 | IPM | MCM | Ethanol | Cyclomethicone 5-NF |
|---|---|---|---|---|---|---|
| | | | Components, % by weight | | | |
| Diclofenac sodium | 1.45 | 15.1 | 7.6 | 8.3 | 17.5 | 50.0 |
| Diclofenac sodium | 1.40 | 7.4 | 4.1 | 4.2 | 58.9 | 24.0 |
| Diclofenac sodium | 1.33 | 9.9 | 4.9 | 4.9 | 78.9 | |
| Hydrocortisone | 0.99 | 24.2 | 12.4 | 13.4 | 49.0 | |
| Hydrocortisone | 0.32 | 9.3 | 4.3 | 5.7 | 20.3 | 60.2 |
| Hydrocortisone acetate | 0.10 | 9.0 | 4.9 | 5.4 | 20.3 | 60.3 |
| Ibuprofen | 4.88 | 25.3 | 12.3 | 12.4 | 45.2 | |
| Ketoprofen | 0.98 | 10.7 | 5.0 | 4.9 | 78.4 | |
| Ketoprofen | 1.90 | 24.5 | 12.2 | 13.9 | 47.5 | |
| Ketoprofen | 2.41 | 9.8 | 5.0 | 5.0 | 19.0 | 58.8 |
| Ketoprofen | 2.60 | 25.5 | 12.4 | 12.4 | 47.1 | |
| Naproxen | 2.05 | 10.7 | 4.9 | 4.9 | 20.0 | 57.4 |
| Naproxen | 2.04 | 25.2 | 12.5 | 12.6 | 47.6 | |
| Sodium fusidate | 2.14 | 3.4 | 9.6 | 9.6 | 19.2 | 56.1 |
| Sodium fusidate | 2.19 | 9.7 | 5.4 | 5.4 | 77.3 | |
| Clindamycin HCl | 1.36 | 25.1 | 12.1 | 12.3 | 49.2 | |
| Clindamycin HCl | 1.06 | 14.8 | 7.1 | 7.2 | 29.0 | 40.7 |

TABLE 11

Pharmaceutical compositions (% w/w) of the invention comprising tacrolimus

|  | KL44a-2 | KL44a-4 | KL44a-5 | KL44b-2 | KL44b-4 | KL44b-5 |
|---|---|---|---|---|---|---|
| Tacrolimus | 1.0 | 1.0 | 1.0 | 1.0 | 1.0 | 1.0 |
| Citric acid | 0.6 |  |  | 0.3 | 0.2 | 0.3 |
| Lipoid S 100 | 10.0 | 10.1 | 15.2 | 10.1 | 9.9 | 15.2 |
| Isopropyl myristate | 5.0 | 5.0 | 2.5 | 5.0 | 4.9 | 2.5 |
| MCM | 5.0 | 5.0 | 2.5 | 5.0 | 4.9 | 2.5 |
| Ethanol | 78.5 | 79.0 | 78.8 | 78.6 | 79.0 | 78.6 |

TABLE 12

Pharmaceutical compositions (% w/w) of the invention comprising curcumin or terbinafine hydrochloride

|  | KL47f-1 | KL47f-2 | KL47f-3 | KL47f-4 | KL48f-1 | KL48f-2 | KL48f-3 |
|---|---|---|---|---|---|---|---|
|  | Curcumin | | | | Terbinafine HCl | | |
| Active | 0.30 | 0.30 | 0.30 | 0.30 | 1.0 | 1.1 | 1.0 |
| Lactic acid |  | 1.5 |  | 1.7 |  |  |  |
| Urea |  |  | 3.3 | 3.2 | 5.0 | 5.3 | 4.2 |
| Lipoid S 100 | 9.5 | 9.5 | 9.5 | 9.5 | 10.0 | 10.4 | 10.4 |
| Isopropyl myristate | 4.7 | 4.7 | 4.7 | 4.7 | 4.9 | 2.8 | 2.5 |
| MCM | 4.7 | 4.8 | 4.7 | 4.7 | 4.9 | 2.5 | 3.3 |
| Ethanol | 80.7 | 79.2 | 77.5 | 75.9 | 74.2 | 77.9 | 78.5 |

TABLE 13

Pharmaceutical compositions (% w/w) of the invention comprising benzocaine, mupirocin, hydrocortisone acetate or vitamin $D_3$

|  | KL48a-2 | KL48a-4 | KL48a-6 | KL48a-8 |
|---|---|---|---|---|
| Active | Benzocaine | Mupirocin | Hydrocortisone acetate | Vitamin $D_3$ |
|  | 5.0 | 0.21 | 0.10 | 0.010 |
| Lipoid S 100 | 14.2 | 14.9 | 14.9 | 14.2 |
| Isopropyl myristate | 7.1 | 7.4 | 7.4 | 7.1 |
| MCM | 7.1 | 7.5 | 7.5 | 7.2 |
| Ascorbic acid | 0.27 | 0.29 | 0.29 | 0.28 |
| Ethanol | 66.3 | 69.7 | 69.7 | 71.2 |

TABLE 14

Pharmaceutical compositions (% w/w) of the invention comprising mometasone furoate

|  | KL48c-1 | KL48c-2 | KL48c-3 | KL48c-4 | KL48c-5 | KL44c-2 | KL44c-4 | KL44c-5 |
|---|---|---|---|---|---|---|---|---|
| Mometasone furoate | 0.10 | 0.10 | 0.10 | 0.10 | 0.10 | 0.10 | 0.10 | 0.10 |
| Lipoid S 100 | 8.9 | 9.0 | 8.9 | 9.2 | 9.0 | 9.93 | 10.01 | 14.78 |
| Isopropyl myristate | 4.6 | 4.5 | 4.6 | 4.6 | 4.6 | 4.93 | 4.97 | 2.45 |
| MCM | 4.4 | 4.5 | 4.5 | 4.6 | 4.5 | 4.95 | 4.99 | 2.46 |
| Propylene glycol | 5.2 | 4.6 | 5.2 | 4.6 | 4.9 |  |  |  |
| Acetic acid | 0.44 | 0.52 |  |  | 0.23 | 0.49 |  | 0.24 |
| Ascorbic acid |  | 0.34 | 0.29 |  | 0.19 |  |  |  |
| Butyl hydroxytoluene |  |  |  |  |  |  | 0.030 | 0.016 |
| Isopropanol |  | 76.4 |  | 76.9 | 38.4 |  |  |  |
| Ethanol | 76.4 |  | 76.4 |  | 38.2 | 79.61 | 79.90 | 79.95 |

TABLE 15

Pharmaceutical compositions (% w/w) of the invention comprising calcipotriol and mometasone furoate

|  | KL48d-1 | KL48d-2 | KL48d-3 | KL48d-4 | KL48d-5 |
|---|---|---|---|---|---|
| Calcipotriol | 0.005 | 0.005 | 0.005 | 0.005 | 0.005 |
| Mometasone furoate | 0.10 | 0.10 | 0.09 | 0.10 | 0.10 |
| Lipoid S 100 | 5.9 | 19.8 |  |  | 6.0 |
| Lipoid H 100 |  |  | 14.9 | 10.0 | 5.9 |
| Lipoid H 50 | 4.1 |  | 7.8 |  | 3.0 |
| Isopropyl myristate | 4.9 |  |  | 5.0 | 2.4 |
| MCM | 4.9 |  |  | 5.0 | 2.4 |
| Ethanol 5-NF | 80.1 | 80.1 | 77.2 | 80.0 | 80.1 |

TABLE 16

Pharmaceutical compositions (% w/w) of the invention comprising dexpanthenol

|  | KL48e-1 | KL48e-2 | KL48e-3 | KL48e-4 | KL48e-5 |
|---|---|---|---|---|---|
| Dexpanthenol | 5.0 | 4.8 | 4.9 | 4.8 | 4.8 |
| Lipoid S 100 | 9.9 |  | 10.0 |  | 5.2 |
| Lipoid H 100 |  | 10.0 |  | 9.9 | 4.7 |
| Ethanol | 44.8 | 45.1 | 75.1 | 75.5 | 60.6 |
| Isopropyl myristate | 5.0 | 5.1 | 5.0 | 4.9 | 4.9 |
| MCM | 5.0 | 5.1 | 5.0 | 4.9 | 4.9 |
| 5-NF | 30.5 | 29.9 |  |  | 14.9 |

TABLE 17

Pharmaceutical compositions (% w/w) of the invention comprising adapalene or clindamycin hydrochloride

|  | KL49f-1 | KL49f-2 | KL49f-5 | KL44e-9 |
|---|---|---|---|---|
| Active | Adapalene |  |  | Clindamycin HCl |
|  | 0.098 | 0.100 | 0.101 | 1.0 |
| Lipoid S 100 | 19.8 |  | 10.2 | 10.1 |
| Lipoid H 100 |  | 19.7 | 10.1 |  |
| Isopropyl myristate | 5.0 | 5.4 | 2.5 | 4.6 |
| MCM | 5.0 | 5.4 | 2.5 | 5.4 |
| Ethanol | 70.2 | 69.3 | 74.6 | 29.0 |
| DMTS |  |  |  | 49.9 |

TABLE 18

Carriers of the invention based on various combinations of lipids and alcohols.

| Component | I | II | III | IV | V | VI | VII | VIII |
|---|---|---|---|---|---|---|---|---|
| Lipoid S 100 |  |  | 10 |  | 20 | 20 | 10 | 10 |
| Lipoid S 75 | 20 |  |  |  |  |  |  |  |
| Dimyristoyl phosphatidylcholine |  | 20 |  |  |  | 10 |  |  |
| Dioleoyl phosphatidylcholine |  |  |  | 10 |  |  |  |  |
| Methyl laurate | 20 | 20 |  |  |  |  |  |  |
| Ethyl oleate |  |  | 20 | 20 |  |  |  |  |
| Isopropyl myristate |  |  |  |  |  | 5 | 5 | 5 |
| Isopropyl palmitate |  |  |  |  | 10 | 5 | 5 |  |
| MCM | 10 | 10 |  |  | 10 | 20 | 20 | 5 |
| Monoolein |  |  | 10 | 10 |  |  |  |  |
| Ethanol | 30 | 30 | 60 | 60 | 20 | 25 | 25 | 80 |
| Isopropanol |  |  |  |  | 40 | 25 | 25 |  |
| 2-Butanol | 20 | 20 |  |  |  |  |  |  |

Examples nos. i) through xi) of cosmetic compositions of the invention are shown in Table 19.

TABLE 19

Cosmetic compositions of the invention

| Composition # | Cosmetically active agent | Lipoid S 75 | Lipoid S 100 | IPM | MCM | Ethanol | 2-Propanol | Butanol |
|---|---|---|---|---|---|---|---|---|
| i | Urea | 4.0 | 30 |  | 10 | 10 | 46 |  |
| ii | Urea | 4.0 |  | 30 | 10 | 10 | 46 |  |
| iii | Urea | 5.0 |  | 30 | 10 | 10 | 35 | 10 |
| iv | Lactic acid | 6.0 |  | 25 | 15 | 15 | 39 |  |
| v | Sodium lactate | 1.0 |  | 30 | 10 | 10 | 49 |  |
| vi | Glycolic acid | 5.0 |  | 30 | 10 | 10 | 45 |  |
| vii | Salicylic acid | 2.0 |  | 30 | 10 | 10 | 38 |  | 10 |
| viii | Urea | 4.8 |  | 10 | 5 | 5 | 73.2 |  |
|  | Glycolic acid | 2.0 |  |  |  |  |  |  |
| ix | Urea | 5.0 |  | 10 | 5 | 5 | 74.9 |  |
| x | Urea | 5.1 |  | 14.9 | 2.5 | 2.5 | 73.8 |  |
|  | Glycolic acid | 1.0 |  |  |  |  |  |  |
| xi | Salicylic acid | 0.5 |  | 9.9 | 5.0 | 5.0 | 79.6 |  |

Example 9. Nicotinate Induced Erythema Development after Application of Carriers of the Invention and Comparative Carriers Circular areas (3.5 cm$^2$) were marked on the volar parts of both forearms of healthy male persons. Baseline measurements of skin color (erythema index, E.I.) were made on the test areas. 18 mm filter papers were soaked with 160 µl of a 0.20% solution of methyl nicotinate in a water/glycerol mixture (4:1). The filter papers were placed in 18 mm Finn Chamber polypropylene coated chambers and attached to the test areas for 5 minutes. After 20 minutes, 10 µl each of carrier VIII of the invention from Table 18 and the comparative carriers listed in Table 20 were evenly distributed on the test areas by the use of a micropipette. E.I. was monitored for about two hours. The average area under the curve (AUC) for ΔE.I. was calculated for comparative carriers I, J, K, L, M and N and for the carrier of the invention VIII. The results are presented in Table 20. Carrier VIII of the invention gave a lower erythema reaction compared to all of the comparative carriers.

TABLE 20

Effect of carriers of the invention and comparative carriers on nicotinate induced erythema.

| Components | Carriers. Components in % by weight | | | | | | |
|---|---|---|---|---|---|---|---|
|  | I** | J** | K** | L** | M** | N** | VIII* |
| Isopropylmyristate | 10 | — | 5 | — | 5 | — | 5 |
| Medium chain monoglycerides | — | 10 | 5 | — | — | 5 | 5 |
| Lipoid S 100 | — | — | — | 10 | 10 | 10 | 10 |
| Ethanol | 90 | 90 | 90 | 90 | 85 | 85 | 80 |
| ΔE.I, AUC 0-2 hours | 4.6 | 3.8 | 4.2 | 4.8 | 4.5 | 3.9 | 3.4 |

*Carrier of the invention;
**Carrier not comprised by the invention

The invention claimed is:

1. Pharmaceutical or cosmetic carrier for topical administration said carrier comprising
   from 2% to 40% by weight of phosphatidylcholine;
   from 2% to 25% by weight of monoglyceride;
   from 2% to 30% by weight of fatty acid ester of $C_1$-$C_3$ alcohol;
   the remainder being volatile solvent at a concentration of at least 25%, the volatile solvent being selected from the group consisting of:
   ethanol; ethanol and $C_3$-$C_4$ alcohol; ethanol and volatile silicone oil; and ethanol, $C_3$-$C_4$ alcohol and volatile silicone oil.

2. The carrier of claim 1, wherein the amount of volatile solvent is in the range of 25% to 90% by weight.

3. The carrier according to claim 1, wherein the amount of $C_3$-$C_4$ alcohol is in the range of 1% to 20% by weight.

4. The carrier according to claim 1, wherein the amount of volatile silicone oil is in the range of 10% to 55% by weight.

5. The carrier according to claim 1, wherein the volatile silicone oil is decamethylcyclopentasiloxane.

6. Pharmaceutical composition comprising:
   a) from 90 to 99.999% by weight of the carrier according to claim 1; and
   b) from 0.001% to 10% by weight of at least one pharmaceutically active agent.

7. Pharmaceutical composition comprising a carrier (a):
   a) from 90% to 99.999% by weight of carrier consisting of:
   from 2% 40% by weight of phosphatidylcholine;
   from 2% 25% by weight of monoglyceride;
   from 2% 30% by weight of fatty acid ester of $C_1$-$C_3$ alcohol;
   the remainder being volatile solvent of a concentration of at least 25%; and
   b) from 0.001% up to 10% by weight of at least one pharmaceutically active agent;
   wherein the weight portions of carrier (a) and at least one pharmaceutically active agent (b) in the composition add up to 100%.

8. The composition of claim 6, wherein the at least one pharmaceutically active agent is selected from the group consisting of: antibacterial agents, antimycotic agents, antiviral agents, antiseptics, anti-inflammatory agents, antiphlogistics/analgesics, antipruritic agents, local anaesthetics, antipsoriatic agents, agents for treatment of eczema and atopic dermatitis, antiglaucomateous agents, agents for erectile dysfunction, anti-dandruff agents, anti-alopecia agents, anti-acne agents, wound healing agents, steroid hormones, and peptide hormones.

9. The composition of claim 6, wherein the at least one pharmaceutically active agent is selected from the group consisting of: calcipotriol, betamethasone or esters thereof, hydrocortisone or esters thereof, mometasone furoate and/or diclofenac or salts thereof.

10. Cosmetic composition comprising a carrier (a):
    a) from 90% to 99.999% by weight of the carrier according to claim 1; and
    b) from 0.001% to 10% by weight of one or more cosmetically active agents.

11. Cosmetic composition comprising a carrier (a):
    a) from 90% to 99.999% by weight of carrier consisting of:
    from 2% 40% by weight of phosphatidylcholine;
    from 2% 25% by weight of monoglyceride;
    from 2% 30% by weight of fatty acid ester of $C_1$-$C_3$ alcohol;
    the remainder being volatile solvent of a concentration of at least 25%; and
    b) from 0.001% to 10% by weight of one or more cosmetically active agent;
    wherein the weight portions of carrier (a) and at least one cosmetically active agent (b) in the composition add up to 100%.

12. The composition of claim 10, wherein the one or more cosmetically active agent is selected from the group consisting of: antiperspirants, sun screens, tanning agents, insects repellants, keratolytics, antidandruff agents, glidants, and moisturizing agents.

13. The composition of claim 10, wherein the one or more cosmetically active agent is selected from the group consisting of urea, glycolic acid, lactic acid, glycerol, propylene glycol and dexpanthenol.

14. Spraying device comprising the composition of claim 6.

15. The carrier of claim 1, wherein the volatile solvent comprises:
    i) up to 50% by weight of $C_3$-$C_4$ alcohol;
    ii) up to 75% by weight of volatile silicone oil; and
    iii) up to 1% of antioxidant, colorant, odorant, preservative and denaturant.

16. The carrier of claim 15, wherein the amount of volatile solvent is in the range of 25% to 90% by weight.

17. The carrier according to claim 15, wherein the amount of $C_3$-$C_4$ alcohol is in the range of 1% to 20% by weight.

18. The carrier according to claim 15, wherein the amount of volatile silicone oil is in the range of 10% to 55% by weight.

19. A pharmaceutical composition comprising:
a) from 90 to 99.999% by weight of the carrier according to claim 15; and
b) from 0.001% to 10% by weight of at least one pharmaceutically active agent.

20. The composition of claim 7, wherein the volatile solvent comprises:
i) up to 50% by weight of $C_3$-$C_4$ alcohol;
ii) up to 75% by weight of volatile silicone oil, and
iii) up to 1% by weight of antioxidant, colorant, odorant, preservative and denaturant.

21. A cosmetic composition comprising:
a) from 90% to 99.999% by weight of the carrier according to claim 15; and
b) from 0.001% to 10% by weight of one or more cosmetically active agents.

22. The composition of claim 8, wherein the antibacterial agents are selected from the group consisting of oxytetracycline, fusidic acid, mupirocin, gentamycine, retapamulin, and pharmaceutically acceptable salts and derivatives thereof; the antimycotic agents are selected from the group consisting of as nystatin, clotrimazole, miconazole, econazole, ketoconazole, bifonazole, and combinations of imidazole and triazole derivatives, ciclopirox, terbinafine, fluconazole, and amorolfine, and pharmaceutically acceptable salts and derivatives thereof; the antiviral agents are selected from the group consisting of aciclovir, valaciclovir, penciclovir, famciclovir, foscarnet and docosanol, and pharmaceutically acceptable salts and derivatives thereof; the antiseptics are selected from the group consisting of chlorhexidine, benzalkonium chloride and hydrogen peroxide; the anti-inflammatory agents are glucocorticoids selected from the group consisting of hydrocortisone, clobetasone, triamcinolone, betamethasone, mometasone, and clobetasol, and pharmaceutically acceptable salts and derivatives thereof; the antiphlogistics/analgesics are selected from the group consisting of acetylsalicylic acid, salicylic acid, diclofenac, ketoprofen, ibuprofen, naproxen, capsaicin, nicotinate, and pharmaceutically acceptable salts and derivatives thereof; the antipruritic agents are glucocorticoids selected from the group consisting of hydrocortisone, clobetasone, clobetasol, desonide, mometasone, and betamethasone; the antipsoriatic agents, are selected from the group consisting of calcipotriol, calcitriol, 7-dehydrocholesterol, cholecalciferol, maxacalcitol, doxercalciferol, paricalcitol, inecalcitol, eldecalcitol, betamethasone, and cyclosporine A, and pharmaceutically acceptable salts and derivatives thereof; the agents for treatment of eczema and atopic dermatitis are selected from the group consisting of tacrolimus and pimecrolimus, and pharmaceutically acceptable salts and derivatives thereof; the antiglaucomateous agents are selected from the group consisting of timolol, betaxolol, latanoprost, bimatoprost, and travoprost, and pharmaceutically acceptable salts and derivatives thereof; the local anaesthetics are selected from the group consisting of lidocaine, prilocaine, ropivacaine, mepivacaine, bupivacaine, levobupivacaine, benzocaine, and tetracaine, and pharmaceutically acceptable salts and derivatives thereof; the agents for erectile dysfunction are selected from the group consisting of alprostadil (prostaglandin E1) and pharmaceutically acceptable salts and derivatives thereof; the anti-dandruff agents are selected from the group consisting of selenium sulphides, piroctone oleamine and ketoconazole; the anti-alopecia agents are selected from the group consisting of minoxidil and pharmaceutically acceptable salts and derivatives thereof; the anti-acne agents are selected from the group consisting of tretinoin (retinoic acid), isotretinoin, adapalene, benzoyl peroxide, clindamycin, azelaic acid, and niacinamide, and pharmaceutically acceptable salts and derivatives thereof; the wound healing agents are selected from the group consisting of pantothenic acid, dexpanthenol, and fusidic acid, and pharmaceutically acceptable salts and derivatives thereof; the steroid hormones are selected from the group consisting of prednisone, dexamethasone, triamcinolone, fludrocortisone, testosterone, estradiol, and distilbestrol; and the peptide hormones are selected from the group consisting of oxytocin, the part LL-37 of the human cathelicidin peptide, and pharmaceutically acceptable salts and derivatives thereof.

23. The composition of claim 12, wherein the antiperspirant, is aluminium chlorohydrate; the sun screens is selected from the group consisting of avobenzone, bemotrizinol, diethylamino hydroxybenzoyl hexyl benzoate, octisalate, octocrylene, and oxybenzone; the tanning agents is dihydroxyacetone; the insects repellants is Deet; the keratolytics are selected from the group consisting of glycolic acid, lactic acid, malic acid, salicylic acid, allantoin, urea and sulphur; and the moisturizing agent is selected from the group consisting of glycerol, sorbitol, dexpanthenol, propylene glycol, butandiols, pentanediols, hexanediols, urea, and lactic acid.

24. Pharmaceutical composition according to claim 6, comprising
a) from 90% to 99.999% by weight of carrier consisting of:
about 10% by weight of enriched phospholipid from soybeans;
about 5% by weight of monoglyceride;
about 5% by weight isopropyl myristate;
the remainder of the carrier being volatile solvent consisting of about 20% by weight ethanol and about 60% by weight cyclomethicone;
b) from 0.001% up to 10% by weight of at least one pharmaceutically active agent;
wherein the weight portions of carrier (a) and at least one pharmaceutically active agent (b) in the composition add up to 100%.

25. Pharmaceutical composition according to claim 24, comprising
a) about 99.995% by weight of carrier consisting of:
about 10% by weight of enriched phospholipid from soybeans;
about 5% by weight of monoglyceride;
about 5% by weight isopropyl myristate;
the remainder of the carrier being volatile solvent consisting of about 20% by weight ethanol and about 60% by weight cyclomethicone;
b) about 0.005% by weight of at least one pharmaceutically active agent;
wherein the weight portions of carrier (a) and at least one pharmaceutically active agent (b) in the composition add up to 100%.

26. Pharmaceutical composition according to claim 24, wherein said at least one pharmaceutically active agent is calcipotriol.

27. Pharmaceutical composition according to claim 24, wherein said at least one pharmaceutically active agent is calcipotriol and glucocorticoid.

* * * * *